(12) United States Patent
Cosman

(10) Patent No.: US 6,675,040 B1
(45) Date of Patent: Jan. 6, 2004

(54) OPTICAL OBJECT TRACKING SYSTEM

(75) Inventor: Eric R. Cosman, Belmont, MA (US)

(73) Assignee: Sherwood Services AG, Schaffhausen (CH)

(*) Notice: Subject to any disclaimer, the term of this patent is extended or adjusted under 35 U.S.C. 154(b) by 0 days.

(21) Appl. No.: 09/491,502

(22) Filed: Jan. 26, 2000

Related U.S. Application Data

(63) Continuation of application No. 09/014,840, filed on Jan. 28, 1998, now abandoned, which is a continuation-in-part of application No. 08/475,681, filed on Jun. 7, 1995, now Pat. No. 6,006,126, which is a continuation-in-part of application No. 08/441,788, filed on May 16, 1995, now Pat. No. 5,662,111, which is a continuation of application No. 08/299,987, filed on Sep. 1, 1994, now abandoned, which is a continuation of application No. 08/047,879, filed on Apr. 15, 1993, now abandoned, which is a continuation of application No. 07/941,863, filed on Sep. 8, 1992, now abandoned, which is a continuation of application No. 07/647,463, filed on Jan. 28, 1991, now abandoned.

(51) Int. Cl.[7] .................................................. A61B 6/00
(52) U.S. Cl. .................... 600/427; 600/429; 600/473; 606/130
(58) Field of Search ................ 600/429, 417, 600/473, 427; 606/130

(56) References Cited

U.S. PATENT DOCUMENTS

| | | |
|---|---|---|
| 3,821,469 A | 6/1974 | Whetsone et al. |
| 3,983,474 A | 9/1976 | Kuipers |
| 4,058,114 A | 11/1977 | Soldner |
| 4,068,156 A | 1/1978 | Johnson et al. |
| 4,068,556 A | 1/1978 | Foley |
| 4,182,312 A | 1/1980 | Mushabac |
| 4,262,306 A | 4/1981 | Renner |
| 4,341,220 A | 7/1982 | Perry |
| 4,358,856 A | 11/1982 | Stivender et al. |
| 4,407,298 A | 10/1983 | Lentz et al. |
| 4,457,311 A | 7/1984 | Sorenson et al. |
| 4,465,069 A | 8/1984 | Barbier et al. |
| 4,473,074 A | 9/1984 | Vassiliadis |
| 4,506,676 A | 3/1985 | Duska |
| 4,571,834 A | 2/1986 | Fraser et al. |
| 4,583,538 A | 4/1986 | Onik et al. |
| 4,592,352 A | 6/1986 | Patil |
| 4,602,622 A | 7/1986 | Bär et al. |
| 4,608,977 A | 9/1986 | Brown |
| 4,638,798 A | 1/1987 | Shelden et al. |

(List continued on next page.)

FOREIGN PATENT DOCUMENTS

| | | |
|---|---|---|
| DE | 295 05 318 U | 5/1995 |
| DE | 297 04 393 U | 7/1997 |
| EP | 0 018 166 | 10/1980 |

(List continued on next page.)

OTHER PUBLICATIONS

Kosugi, Yukio et al., "An Articulated Neurosurgical Naviation System Using MRI and CT Images", *IEEE Transactions on Biomedical Engineering*, vol. 35, No. 2, pp. 147–152, Feb. 1988.

(List continued on next page.)

*Primary Examiner*—Ruth S. Smith

(57) ABSTRACT

Camera systems in combination with data processors, image scan data, and computers and associated graphic display provide tracking of instruments, objects, patients, and apparatus in a surgical, diagnostic, or treatment setting. Optically detectable objects are connected to instrumentation, a patient, or a clinician to track their position in space by optical detection systems and methods. The recognition of instruments by patterns of optically detectable structures provides data on three-dimensional position, orientation, and instrument type. Passive or active optical detection is possible via various light sources, reflectors, and pattern structures applicable in various clinical contexts.

49 Claims, 5 Drawing Sheets

U.S. PATENT DOCUMENTS

| | | | |
|---|---|---|---|
| 4,645,343 A | 2/1987 | Stockdale et al. | |
| 4,651,732 A | 3/1987 | Frederick | |
| 4,659,971 A | 4/1987 | Suzuki et al. | |
| 4,660,970 A | 4/1987 | Ferrano | |
| 4,674,057 A | 6/1987 | Caughman et al. | |
| 4,686,997 A | 8/1987 | Oloff et al. | |
| 4,698,777 A | 10/1987 | Toyoda et al. | |
| 4,701,049 A | 10/1987 | Beckmann et al. | |
| 4,701,407 A | 10/1987 | Appel | |
| 4,705,395 A | 11/1987 | Hageniers | |
| 4,705,401 A | 11/1987 | Addleman et al. | |
| 4,706,665 A | 11/1987 | Gouda | |
| 4,709,156 A | 11/1987 | Murphy et al. | |
| 4,722,056 A | 1/1988 | Roberts et al. | |
| 4,723,544 A | 2/1988 | Moore et al. | |
| 4,733,661 A | 3/1988 | Palestrant | |
| 4,733,969 A | 3/1988 | Case et al. | |
| 4,737,032 A | 4/1988 | Addleman et al. | |
| 4,742,815 A | 5/1988 | Ninan et al. | |
| 4,743,770 A | 5/1988 | Lee | |
| 4,743,771 A | 5/1988 | Sacks et al. | |
| 4,745,290 A | 5/1988 | Frankel et al. | |
| 4,750,487 A | 6/1988 | Zanetti | |
| 4,753,128 A | 6/1988 | Bartlett et al. | |
| 4,753,528 A | 6/1988 | Hines et al. | |
| 4,761,072 A | 8/1988 | Pryor | |
| 4,762,016 A | 8/1988 | Stoughton et al. | |
| 4,764,016 A | 8/1988 | Johansson | |
| 4,776,749 A | 10/1988 | Wanzenberg et al. | |
| 4,779,212 A | 10/1988 | Levy | |
| 4,791,934 A | 12/1988 | Brunnett | |
| 4,794,262 A | 12/1988 | Sato et al. | |
| 4,797,736 A | 1/1989 | Kloots et al. | |
| 4,805,615 A | 2/1989 | Carol | |
| 4,809,694 A | 3/1989 | Ferrara | |
| 4,821,200 A | 4/1989 | Oberg | |
| 4,821,206 A | 4/1989 | Arora | |
| 4,822,163 A | 4/1989 | Schmidt | |
| 4,825,091 A | 4/1989 | Breyer et al. | |
| 4,829,373 A | 5/1989 | Leberl et al. | |
| 4,835,710 A | 5/1989 | Schnelle et al. | |
| 4,836,778 A | 6/1989 | Baumrind et al. | |
| 4,841,967 A | 6/1989 | Chang et al. | |
| 4,859,181 A | 8/1989 | Neumeyer | |
| 4,875,478 A | 10/1989 | Chen | |
| 4,896,673 A | 1/1990 | Rose et al. | |
| 4,931,056 A | 6/1990 | Ghajar et al. | |
| 4,933,843 A | 6/1990 | Scheller et al. | |
| 4,941,164 A * | 7/1990 | Schuller et al. | 378/205 |
| 4,943,296 A | 7/1990 | Funakubo et al. | |
| 4,945,914 A | 8/1990 | Allen | |
| 4,954,043 A | 9/1990 | Yoshida et al. | |
| 4,955,891 A | 9/1990 | Carol | |
| 4,961,422 A | 10/1990 | Marchosky et al. | |
| 4,991,579 A | 2/1991 | Allen | |
| 5,016,639 A | 5/1991 | Allen | |
| 5,017,139 A | 5/1991 | Mushabac | |
| 5,027,818 A | 7/1991 | Bova et al. | |
| 5,047,036 A | 9/1991 | Koutrouvelis | |
| 5,050,608 A | 9/1991 | Watanabe et al. | |
| 5,078,140 A | 1/1992 | Kwoh | |
| 5,080,662 A | 1/1992 | Paul | |
| 5,086,401 A | 2/1992 | Glassman et al. | |
| 5,094,241 A | 3/1992 | Allen | |
| 5,097,839 A | 3/1992 | Allen | |
| 5,099,836 A | 3/1992 | Rowland et al. | |
| 5,107,839 A | 4/1992 | Houdek et al. | |
| 5,119,817 A | 6/1992 | Allen | |
| 5,142,930 A | 9/1992 | Allen et al. | |
| 5,186,174 A | 2/1993 | Schlöndorff et al. | |
| 5,193,106 A | 3/1993 | DeSena | |
| 5,197,476 A | 3/1993 | Nowacki et al. | |
| 5,207,223 A | 5/1993 | Adler | |
| 5,211,164 A | 5/1993 | Allen | |
| 5,224,049 A | 6/1993 | Mushabac | |
| 5,230,338 A | 7/1993 | Allen et al. | |
| 5,251,127 A | 10/1993 | Raab | |
| 5,295,483 A * | 3/1994 | Nowacki et al. | |
| 5,305,203 A | 4/1994 | Raab | |
| 5,383,454 A | 1/1995 | Bucholz | |
| 5,389,101 A | 2/1995 | Heilbrun et al. | |
| 5,436,542 A * | 7/1995 | Petelin et al. | |
| 5,446,548 A | 8/1995 | Gerig et al. | |
| 5,526,812 A * | 6/1996 | Dumoulin et al. | 600/407 |
| 5,617,857 A | 4/1997 | Chader et al. | |
| 5,622,170 A | 4/1997 | Schulz | |

FOREIGN PATENT DOCUMENTS

| | | |
|---|---|---|
| EP | 0 062 941 | 10/1982 |
| EP | 0 326 768 | 8/1989 |
| EP | 0 359 773 | 3/1990 |
| EP | 0 629 963 | 12/1994 |
| EP | 0 672 389 | 9/1995 |
| FR | 2417-970 | 10/1979 |
| GB | 2 094 590 | 9/1982 |
| WO | WO 90/05494 | 5/1990 |
| WO | WO 91/07726 | 5/1991 |
| WO | WO 96 11624 | 4/1996 |
| WO | WO 97 45064 | 12/1997 |
| WO | WO 97 47240 | 12/1997 |

OTHER PUBLICATIONS

Adams, Ludwig et al., "Computer–Assisted Surgery", *IEEE Computer Graphics & Applications,* pp. 43–51, May 1990.

Gonzalez, Rafael C., et al. "Stereo Imaging", *Digital Image Processing,* Second Edition, Addison–Wesley Publishing Company, Section 2.5.5, pp. 52–54 (Section from a Book).

Wolff, Robert S., et al., "Through Canyons and Planets", *Visualization of Natural Phenomena,* First Edition, TELOS the Electronic Library of Science, Santa Clara, California, Chapter 3, pp. 66–67 (Chapter from a Book).

Wolfe, William L., et al., "Image Trackers", *The Infrared Handbook,* Environmental Research Institute of Michigan for the Office of Naval Research, 1978, pp. 22–63—22–67 and 22–74—22–77 (Chapter from a Book).

Castleman, Kenneth R., "Stereometric Ranging", *Digital Image Processing,* Prentice–Hall, Inc., Englewood Cliffs, New Jersey 1979, pp. 364–369 (Chapter from a Book).

Foley, James D., et al., "Geometrical Transformations", *Fundamentals of Interactive Computer Graphics,* Second Edition, Addison–Wesley Publishing Company, 1984, Chapter 7, pp. 245–266 (Chapter from a Book).

Newman and Sproull, "Moving Parts of An Image", *Principles of Interactive Computer Graphics,* McGraw–Hill Book, Company, 1979, Section 17, p. 254 (Section from a Book).

* cited by examiner

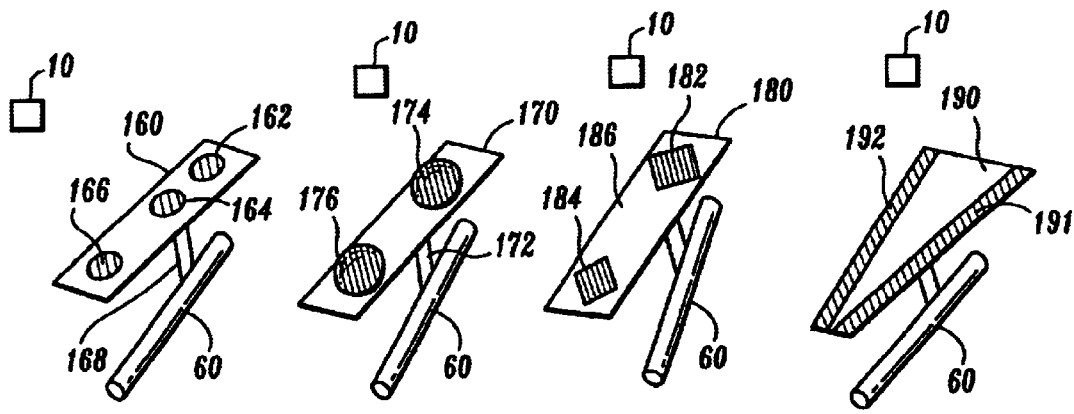
FIG. 3A  FIG. 3B  FIG. 3C  FIG. 3D
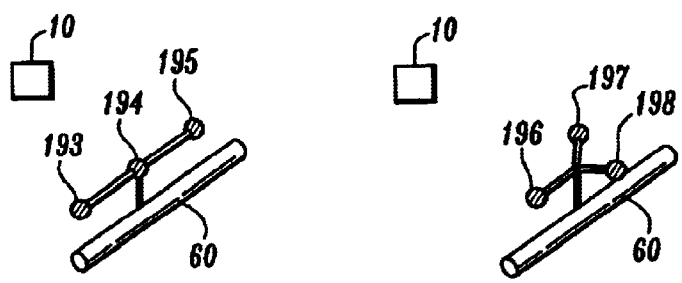
FIG. 3E  FIG. 3F
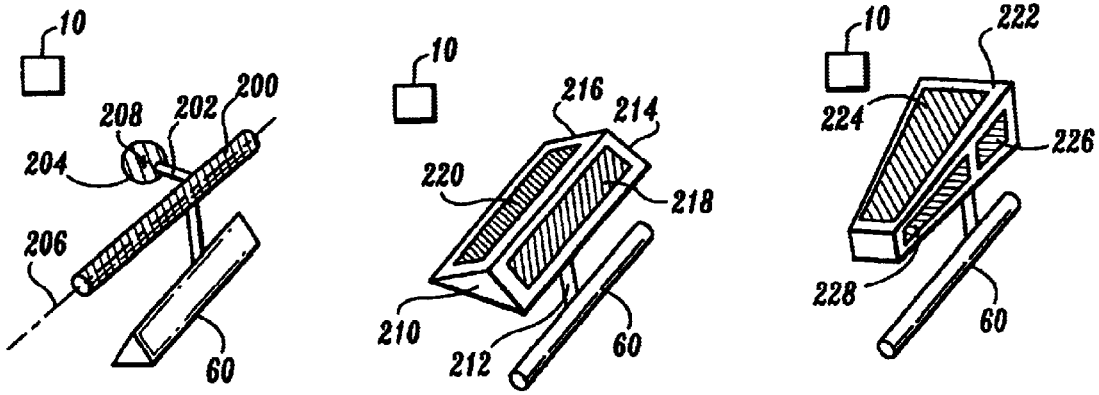
FIG. 4A  FIG. 4B  FIG. 4C

OPTICAL OBJECT TRACKING SYSTEM

CROSS-REFERENCES

This is a continuation of application Ser. No. 09/014,840, filed on Jan. 28, 1998 now abandoned, which is a continuation-in-part of application Ser. No. 08/475,681, filed on Jun. 7, 1995, U.S. Pat. No. 6,006,126, which is a continuation-in-part of application Ser. No. 08/441,788, filed on May 16, 1995, U.S. Pat. No. 5,662,111, which is a continuation of application Ser. No. 08/299,987, filed Sep. 1, 1994, now abandoned, which is a continuation of application Ser. No. 08/047,879, filed Apr. 15, 1993, now abandoned, which is a continuation of application Ser. No. 07/941,863 filed on Sep. 8, 1992, now abandoned, which is a continuation of application Ser. No. 07/647,463 filed on Jan. 28, 1991, now abandoned.

FIELD OF THE INVENTION

The invention relates generally to medical equipment used in the surgical treatment of disease, and more particularly to a system and method for medical instrument navigation by optically tracking the positions of instruments used during surgery or other treatments in relation to a patient's anatomy.

BACKGROUND OF THE INVENTION

Image guided stereotaxy is widely used in the field of neurosurgery. It involves the quantitative determination of anatomical positions based on scan data taken from a CT, MRI or other scanning procedures to obtain three-dimensional scan data. Typically, the image scan data is placed in a computer to provide a three-dimensional database that may be variously used to provide graphic information. Essentially, such information is useful in surgical procedures and enables viewing a patient's anatomy in a graphics display.

The use of image guided stereotactic head frames is commonplace. For example, see U.S. Pat. No. 4,608,977 issued Sep. 2, 1986 and entitled, System Using Computed Tomography as for Selective Body Treatment. Such structures employ a head fixation device typically with some form of indexing to acquire referenced data representative of scan slices through the head. The scan data so acquired is quantified relative to the head frame to identify individual slices. A probe or surgical instrument may then be directed to an anatomical feature in the head by mechanical connection to the head frame based on scan data representations. Three-dimensional scan data has been employed to relate positions in a patient's anatomy to other structures so as to provide a composite graphics display. For example, a mechanically linked space pointer (analogous to a pencil) attached to the end of an encoded mechanical linkage might be directed at a patient's anatomy and its position quantified relative to the stereotactic scan data. The space pointer might be oriented to point at an anatomical target and so displayed using computer graphics techniques. Such apparatus has been proposed, using an articulated space pointer with a mechanical linkage. In that regard, see an article entitled "An Articulated Neurosurgical Navigational System Using MRI and CT Images," IEEE Transactions on Biomedical Engineering, Volume 35, No. Feb. 2, 1988 (Kosugi, et al.) incorporated by reference herein.

The above-described systems have at least two disadvantages of note. First, the head frame and the articulated space pointer are mechanically connected to an apparatus used to measure and calculate the position of the probe or pointer. Consequently, although a relatively high number of degrees of freedom can be provided to the pointer (or other tool coupled to the pointer), the mechanical linkage may still restrict the possible ranges of motion available to the clinician. Furthermore, the linkages may be large and obtrusive, and can be difficult to sterilize.

Second, although the apparatus tracks the position of the space pointer in relation to the patient's anatomy, the clinician is still free to move about the patient and operate from any desired position. This is not reflected by the data produced by the device. Accordingly, although a "pointer's eye" view of the surgical field can be provided, if the clinician is operating from any of various other angles, then any graphical representation of the surgical field may be disorienting, confusing, or not representative of the "surgeon's eye" view. Although the system's point-of-view might be selected and altered manually, this is not an optimum solution, as it requires additional steps to be taken by the clinician or an assistant.

In light of the above considerations, the need for relating external treatment apparatus or surgical viewing directions to a specific target arises in several aspects. For example, the need arises in relation to the treatment of internal anatomical targets, specifically to position and maintain such targets with respect to a surgical instrument such as a probe, a microscope with a specific direction and orientation of view, or an X-ray treatment beam associated with a large external apparatus. Thus, a need exists for methods for aligning a surgical instrument, probe, or beam not attached by any mechanical linkage, to impact specific anatomical targets via a path selected to avoid injury to other critical anatomical structures. A further need exists for the capability to show the operating clinician a view of the patient's anatomy and the surgical tool from a perspective that is natural to the clinician, and not disorienting or confusing. Further, there is a need for an economic, compact, and wireless system and method to track instruments in clinical applications.

SUMMARY OF THE INVENTION

Generally, in accordance herewith, an optical camera apparatus functions in cooperation with a computer system and a specially configured surgical instrument. In an embodiment of the invention, the camera system is positioned to detect a clinical field of view and to detect index markers on a surgical instrument, a patient, and/or a surgeon. The markers are tracked by the camera apparatus. The image scan data (such as from a CT or MR scan of the patient's anatomy) and data specifying the position of the instrument and the surgeon are transformed relative to the patient's anatomy and the camera coordinate system, thereby aligning the scan data, patient position and orientation data, instrument position and orientation data, and surgeon position and orientation data for selectable simultaneous viewing on a computer display.

Various exemplary embodiments are given of the use of lines, arrays of points, geometric patterns and figures, lines of light, and other optically detectable marker configurations to identify the position and orientation of a surgical instrument, a patient, and a surgeon. The disclosed embodiments have the advantage of being wireless and optically coupled to the camera tracking system. Moreover, they can be relatively economical and lightweight in comparison to the mechanically coupled tracking devices described in the background section above. Once the positions of the instrument, patient, and surgeon have been determined with respect to a common coordinate system, a simulated view of the instrument and the patient can be provided on a display device in a manner that is comfortable and convenient to the surgeon. In an embodiment of the invention, the simulated view is overlaid with an actual live video display to further orient the surgeon.

BRIEF DESCRIPTION OF THE DRAWINGS

In the drawings, which constitute a part of this specification, embodiments are exhibited in various forms, and are set forth specifically:

FIG. 2, which includes

FIG. 3, which includes FIGS. 3A, 3B, 3C, 3D, 3E, and 3F, illustrates various optically detectable objects attached to instruments in accordance with the present invention;

FIG. 4, which includes FIGS. 4A, 4B, and 4C, illustrates additional alternative embodiments of optically detectable objects in accordance with the present invention;

DETAILED DESCRIPTION OF THE INVENTION

Figure 1:
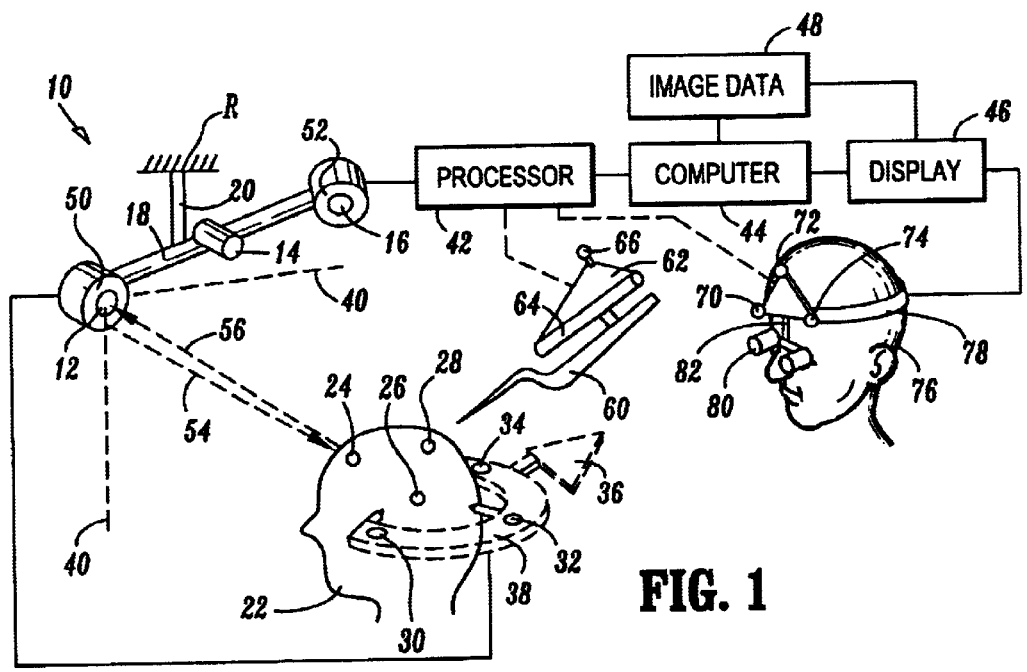
FIG. 1 schematically illustrates a system for optically tracking instruments and other objects in a surgical field in accordance with the present invention.

Referring initially to FIG. 1, an embodiment of a system according to the invention is shown schematically as including a camera system 10 that has a field of view Hi that includes multiple elements. The elements can include a surgical field for surgical application or a treatment field for therapy applications. Part of the patient's body 22 may or may not be in the camera field. Mounted to the patient within the camera field are several optically detectable objects such as markers 24, 26, and 28, which are mounted directly on the patient, or alternatively, identifiers 30, 32, 34, and 36 connected to a structure 38 that is rigidly connected to the patient's body 22.

The markers 24, 26, and 28 or the identifiers 30, 32, 34, and 36 may be light-emitting, light-reflecting, or otherwise optically differentially detectable geometric structures, patterns, or elements. They may comprise, for example, light-emitting diodes ("LEDs") capable of emitting infrared, visible, or other wavelengths of light; reflectors, such as mirrors, reflective paint, reflective sheeting or tape, reflective dispersions, and so on. The markers or identifiers may be fabricated in any of various shapes including discs, annular plates or rings, domes, hemispheres, spheres, triangles, squares, cubes, diamonds, or combinations thereof. It has been found that circular stick-down circles, domes or spheres are usable in this application.

The identifier 36 may include a reflective surface of triangular shape, for example, that is detectable in spatial position and orientation by the camera system 10. In this way, the patient's position and orientation can be detected with respect to the coordinate system of the camera system 10; this procedure will be discussed in further detail below.

The camera system 10 comprises one or more cameras, each of which can be selected from optical cameras of various known types. In FIG. 1, three cameras are shown as part of the camera system 10. In the disclosed embodiment, a right-mounted camera 12 and a left-mounted camera 16 are capable of resolving two-dimensional images. The dashed lines 40 illustrate the field of view of the right-mounted camera 12; the left-mounted camera 16 has a similar (but displaced) field of view. The cameras provide optical camera data to processor 42 related to optically detectable objects in the common field-of-view of the cameras included in the camera system 10. For example, for the multiple-camera system 10 including cameras 12 and 16, stereoscopic or three-dimensional position data on the optically detectable object positions in the coordinate camera system can be derived by the processor 42. Thus, in accordance with the invention, the positions and orientations of objects within the camera system field of view can be determined rapidly by the processor 42 and sent to a computer 44. As will be discussed in further detail below, the computer 44 has software to represent the positions and orientations of those objects in camera coordinates and display the objects in various representations on a display means 46 as desired by the clinician.

Considering now the structure of the camera system 10, a lateral support 18 for the cameras 12 and 16 is fixed by a coupler 20 to a rigid reference R, such as the ceiling, wall, or floor of a room. Also shown in FIG. 1 are light sources 50 and 52, which in the disclosed embodiment are mounted in proximity to cameras 12 and 16, respectively. These light sources can send light outward as for example along a path represented by a dashed line 54 to be reflected off of a reflective optically detectable object such the marker 24 on the patient's body 22. Reflected light then returns along a path such as that represented by a dashed line 56, and is detected by the camera 12.

If the marker 24 and other markers and identifiers in the field include reflective surfaces, points, lines, or regions, then these structures can be represented as camera data in a three-dimensional coordinate system fixed with respect to the camera system 10. For example, in one embodiment of the invention, the light sources 50 and 52 are be pulsed clusters of LEDs in the infrared (IR) frequency range, and cameras 12 and 16 have selective IR filters matched to the IR source wave length. Thereby, a good signal-to-noise of reflected light to ambient light is achievable, and good discrimination of the markers and other identifiers (such as markers 24, 26, and 28 and identifiers 30, 32, 34, and 36) is possible.

Alternatively, ambient lighting conditions can be used to enable cameras 12 and 16 to detect the markers and identifiers. If the marker 24, for example, is a brightly colored (white, green, red, etc.) disc, sphere, or other shape that stands out in contrast to whatever is visible in the background, then the marker's position can be detected by the cameras. For example, if the identifier 30 is bright white, and the surface of head clamp structure 38 is dark or black, then the identifier 30 can be discriminated by the camera system 10.

As stated above, one or more cameras may be used in the camera system 10. As is well known in the art, two or more cameras will yield stereoscopic data on objects in the clinical field of view in relation to the camera frame of reference or in camera coordinates.

In an alternative embodiment of the invention, some or all of the optically detectable identifiers (such as identifiers 30, 32, and 34) may comprise light sources themselves. For example, the identifiers may be LEDs or other powered light sources such as lamps, possibly enclosed in diffusing globes. The light elements of identifiers 30, 32, and 34 can be triggered by and synchronized with cameras 12 and 16. In this embodiment, electronic shutters in the cameras can be used to enable the camera detectors at just the time when elements 30, 32, and 34 illuminate, thereby increasing the signal-to-noise ratio.

Also shown in FIG. 1 is a surgical instrument 60. The instrument can be of any known surgical type, including but not limited to probes, cutting devices, suction tubes, endoscopes, electronic probes, and other tools. Attached to the instrument 60 is at least one optically detectable element 62, which can comprise various geometric structures that are detectable and recognizable by cameras 12 and 16. For example, in the embodiment disclosed in FIG. 1, a rod indicator 64 is shown in a fixed relationship with a spherical indicator 66.

As discussed above, these indicators 64 and 66 can comprise reflective material, bright or colored surfaces, or light-emitting elements which are detected by cameras 12 and 16. The three-dimensional position and orientation of the element 62 can then be calculated using the camera data processor 42 and the computer 44. The orientation and position of the instrument 60 can thereby be determined. A calibration or pre-fixed position of the element 62 with respect to the instrument 60 may be performed before surgery or intraoperatively (see, for example, several of the products of Radionics, Burlington, Mass.). As with the other markers and indicators, if indicators 64 and 66 are light emitting, they can be connected the processor 42 (dashed line), and synchronized to strobing of the camera system 10.

In addition, light-detectable indicators 70, 72, and 74 are shown on a surgeon 76. In the disclosed embodiment, the indicators 70, 72, and 74 are attached to a headband 78 worn by the surgeon 76. This optical detectable array can then be tracked by the camera system 10 along with the patient's body 22 and the instrument 60. The camera data processed in the processor 42 and assimilated in the computer 44 can thereby track in three-dimensional space relative to the camera system 10 the positions of all elements and their relative orientations. Thus, for example, when the indicators 70, 72, and 74 are light-emitting, the processor 42 can be connected to the surgeon's headband 78 (dashed line) to synchronize the indicators' signals.

By tracking the surgeon 76 via the headband 78, image data can be provided to the surgeon 76 via an optical headset 80 worn by the surgeon. For example, in the disclosed embodiment, the optical headset 80 is a binocular magnifier with built-in image-splitting elements. Graphic data from the processor 42, originating from image scan data 48 pre-scanned from the patient 22, can be sent into the viewing elements of the headset 80 to update the surgeon 76 with location data correlated to the surgeon's viewing position. For example, from the surgeon's eye view, as represented by the position defined by indicators 70, 72, and 74, a reconstructed image of CT or MRI data taken previously and provided to the computer 44 can be displayed via the headset 80, thereby permitting the surgeon 76 to see a "reconstructed" view from the direction of his physical perspective. The computer 44 can assimilate historic image data 48 and convert it to reconstructed planar images and send that information to a display element 46, which thereafter can be "piped" or transmitted to the headset 80 for the surgeon's use.

Alternatively, the headset 80 can comprise at least one video camera 82 capable of viewing the surgical field from the surgeon's direction. Information from the video camera 82 can be sent (via the dashed line) to the processor 42 and the computer 44 and onto the display 46. Once again, that information can then be reconstructed and displayed via a split screen prism in the surgeon's field-of-view via his headset 80. The surgeon's view information can be oriented in a suitable direction by the tracking of the indicators 70, 72, and 74 with the camera system 10, as discussed above. Thus, the video information displayed in the headset 80 can be rendered from stereotactic camera coordinates.

The processor 42, in one embodiment of the invention, is a dedicated processor for electronic data from the camera system 10. The processor 42 is also capable of synchronously controlling the light emitters 50 and 52, if needed to illuminate the optically detectable markers or indicators on the patient 22, the head holder structure 38, the instrument 60, or the surgeon 76. Data from the processor 42 is sent to the computer 44, where it is then analyzed in three-dimensional camera-based coordinates. Image data 48 can be in memory of the computer 44 or otherwise transferred to computer 44, as for example optical disk, magnetic tape, etc. The visualization of camera data and image scan data (CT, MR, PET, ultrasound, etc.) is accomplished via the display 46, which in various embodiments can be a CRT, liquid crystal display, heads-up display, or other display device.

The visual image presented by the display 46 represents the position of the instrument 60 in terms of orientation, tip position, and other characteristics with respect to the image scan data 48 in a variety of ways. For examples, see documentation for the OTS product of Radionics, Burlington, Mass. Specifically, cataloging slices, probe view, in-probe reconstructions, three-dimensional wedge views, and other views of the instrument 60 relative to the patient 22 can be represented on the display 46. Also, the surgeon's view, via registration of the visual headset 80 (by identifying the indicators 70, 72, and 74 as described above) can also be shown on the display 46. Although the instrument 60 is schematically shown as a pointed instrument in FIG. 1, it should be noted that an instrument 60 for use with the present invention can be nearly any surgical instrument or device, such as a microscope, an endoscope, a cutting instrument, an ultrasonic imaging probe, or a treatment device such as an X-ray collimation device for a linear accelerator (LINAC). There are many other possibilities, as well.

The objects in this field of view of the camera system 10 can be tracked in the three-dimensional coordinate space of the camera system 10. The instrument 60 can be calibrated relative to the patient 22 in a variety of ways (see the OTS Tracking System of Radionics, Burlington, Mass. for examples). In one embodiment of the invention, during a calibration procedure, the instrument 60 is touched to a plurality of fiducial markers placed on the patient 22 (for example, the markers 24, 26, and 28), natural landmarks on the patient's skin, surface swabbing of the patient's anatomy, a reference to real-time imaging data (for example ultrasound, MRI, CT, etc.) in the situation where the structure 38 is connected or associated with such an imaging apparatus, and so on. As stated, the processor 42 (or the computer 44) uses such data in a calibration step so that the position of the instrument 60 is in a known position and orientation relative to the patient 22 or the structure 38 affixed to the patient 22, or even with respect to apparatus elsewhere in the room such as a linear accelerator, an image scanner, or an apparatus on a surgeon (the headband 78, for example).

Referring now to FIG. 2, various embodiments of patterns, shapes, and objects for the optically detectable elements that can be used on, for example, the instrument 60 (FIG. 1) or the patient 22, the surgeon 76, a microscope, or other surgical device not shown. In FIG. 2A, the surgical instrument 60 is rendered schematically. Although the instrument 60 is depicted in the embodiment set forth in FIG. 2, it should be noted that similar or identical configurations can be used on the patient 22, the structure 38, the surgeon 76, or any other implement to be tracked. In the disclosed embodiment, the instrument 60 has a surgical axis (dashed line 84) and a focal point, end point, isocenter, or other characteristic point 86. It can have other independent axes such as those illustrated by dashed lines 85 and 87 to describe its orientation if it is, for example, a rigid body. In FIG. 2A, a geometric object 88, specifically a triangle, is attached to the instrument 60 by a connector 90. In the illustrated embodiment, the connector 90 is a rigid coupling and is in a predetermined relationship with the instrument 60; alternatively, it could be in an arbitrary relationship with the instrument 60 and subject to calibration. The geometric 88 bears a bright portion 92 (the hatched area) on its surface. The bright portion 92 of the surface of the geometric object 88 may comprise reflective paint, reflective film, a brightly colored surface in a particular color spectrum, or an illuminated field. The camera system 10 is represented here only schematically, but could comprise the elements described in FIG. 1, including cameras, light sources, a processor, a computers, image data, and a display, among other items. Further, it should be noted that although the geometric object 88 and its bright portion 92 are specifically described and shown as triangular in configuration, many other shapes are possible and equally operative in the context of the invention, which is not so limited.

The position and orientation of the instrument 60 can be determined by tracking the position and orientation of the geometric object 88. In various forms, the instrument 60 may be a rigid body of complex shape. Its position, for example, may be characterized by axes such as 84, 85 and 87, and its orientation around an axis 84 may be characterized by a rotation angle indicated by an arrow 83. By calibrating the geometric object 88 to the instrument 60, this rotation angle 83 and the position and orientation of the axes 84, 85, and 87 may be tracked relative to the coordinate system of the camera system 10. This can be done by rigid body transformations which are well known to those skilled in matrix mathematics. Thus, for example, if the instrument 60 is an endoscope or a microscope for which the axis 84 represents a viewing direction, the characteristic point 86 is a point desired to be viewed in the surgical field, then rotation angle 83 with the axes 85 and 87 represent the orientation of the viewing field relative to the patient's coordinate system or the coordinate system of image scan data, then tracking the geometric object 88 will provide position and orientation tracking of the endoscopic or microscopic field of view.

Detecting the edges of the bright portion 92 in the three-dimensional coordinate system relative to the camera system 10 enables the direction and orientation of the geometric object 88 to be determined. By calibrating or precalibrating the orientation of the geometric object 88 relative to the instrument 60, specifically its axis 84 and characteristic point 86 (including other axes such as axes 85 and 87, if necessary), tracking of the instrument 60 can be accomplished (see for example the OTS Optical Tracking System of Radionics, Burlington, Mass.). The camera system 10, the processor 42, and the computer 44 (FIG. 1) are adapted to detect edges such as a line 94 between the bright portion 92 and the remainder of the geometric object 88, as well as the other respective edges of the triangle or geometric shape. This may be accomplished by differential detection of the shaded area of the triangle versus the perimeter band, which may not be of reflective, brightly colored, or illuminating optically detectable material. Edge detection of geometric shapes can be done by well-known segmentation or detection algorithms in the processor 42 or the computer 44. Three non-collinear points define a plane; additional data can be used to define position and orientation within the plane.

Figure 2A:
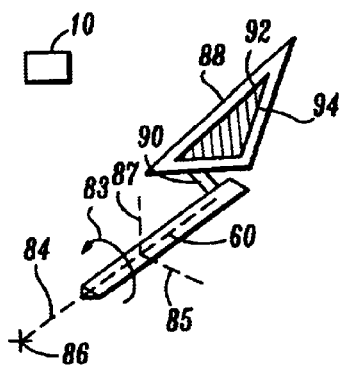
FIGS. 2A, 2B, 2C, 2D, 2E, 2F, 2G, and 2H, illustrates various configurations of optically detectable geometric objects and patterns associated with objects to be tracked in accordance with the system of FIG. 1.
Figure 2B:
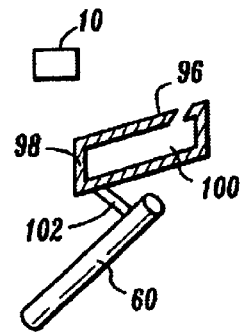

Referring now to FIG. 2B, another type of index structure is shown. The index structure comprises a four-sided geometric shape 96 having a shaded band 98 which may be of reflective or bright material. Inside is a relatively dark area 100 which may be of non-reflective material. Alternatively, the roles of the shaded band 98 and dark area 100 could be reversed. The camera system 10 detects this object and the linear edges of the band 98 or the dark area 100. This establishes the position and orientation of the shape 96. As with the other index structures disclosed herein, the shape 96 is attached by a connector 102 to the instrument 60.

Such a shape 96 could be easily made. The differentially reflective areas (i.e., the shaded band 98 and the dark area 100) can be sprayed on, etched, or deposited on by a masking process; any of these procedures would be inexpensive and lead to very sharp linear borders between the two regions. These borders can then be detected by the camera system 10 via linear discrimination algorithms in the processor 42 and the computer 44 (FIG. 1). If the shape 96 is a parallelogram or a square, the orientation of the plane of the shape 96 can easily be determined by vector cross-product calculations of the linear positions of the borders in three-dimensional space with the edges of the object. As with all the examples in FIG. 2, the connector 102 is optional; if the shape 96 is integrally part of the tool or instrument 60, viz. part of its handle, then an explicit connector 102 would not be needed.

Figure 2C:
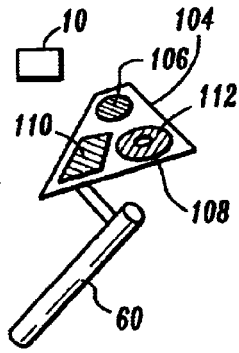

Referring to FIG. 2C, the instrument 60 has attached to it an optically detectable shape 104 in the form of a solid or a plate. On it are various geometric patterns 106, 108, and 110, which may be, for example, reflective patches or painted areas on a black background. These structures by their respective shapes and orientation encode the position and orientation of the shape 104. The patterns can be circles, domes, spheres, or ellipsoids which are detectable by the camera system 10. The shape 104 may be flat or curved, according to needs. In an embodiment of the invention, one of the patterns, e.g. pattern 110, has a more linear structure which is distinguishable from curvilinear shapes such as shapes 106 and 108 also identifiable by the camera system 10. In this embodiment, the pattern 108 has an annular shape with a hole 112 in the middle to distinguish it from a dot-shaped pattern 106. The combination can uniquely identify and locate the shape 104, and therefore the instrument 60, in its orientation and position. The various patterns 106, 108, and 110 can be distinguished from each other, from the background, and from other types of surgical instruments by their reflectivity, color, position, and geometry to give a unique signature or knapping to the instrument 60. For example, the tool could be a special forceps, and the shape 104 with its distinguishing optical characteristics, could be known to the camera system 10 and its associated computer system 44 to be a particular type of forceps. Similarly, other specific tools can have different optically detectable signature structures.

Figure 2D:
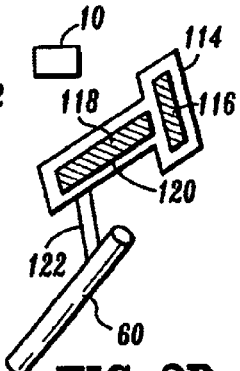

Referring to FIG. 2D, a flat detectable shape 114 is shown. The shape 114 has orthogonal bar patterns 116 and 118, which could be again reflective tape on a black background of the shape 114. These patterns are recognizable and distinguishable by detecting the borders, such as a line 120 between the patterns 116 and 118 and the background. Linear structures are easily detectable by camera systems and pattern recognition software. The camera system 10 could easily scan such a geometric linear pattern in distinguishing the linear bar patterns, thereby determining the orientation of the patterns 116 and 118 as orthogonal and in a given spatial three-dimensional position. The orientation of the shape 114 and its position in space can be determined in the coordinates of the camera system 10. A fixed relationship between the instrument 60 and the shape 114 via a connector 122 can then be used to identify the position and orientation of the instrument 60 in all of its movements within the field of view of the camera system 10.

Figure 2E:
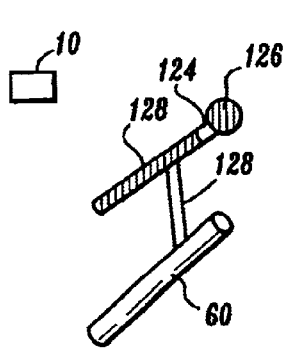

FIG. 2E shows yet another embodiment of the present invention with shows a linear rod 124 and a spherical object 126 coupled together. For instance, a reflective surface 128 on the rod 124 (shaded in the drawing) could be taped or painted onto the rod 124. On the end of the rod, the spherical object 126 bearing reflective tape or paint is, in the disclosed embodiment, coaxial with the painted surface 128 of the rod 124. The camera system 10 is capable of recognizing the linear form of the rod 124 and the center of the spherical object 126. Accordingly, a detection algorithm in the computer 44 (FIG. 1) could determine the linear configuration and central axis of the rod 124, and the centroid point of the spherical object 126, thereby determining a vector direction along the axis of the rod 124 and a uniquely identified endpoint at the spherical object 126. The rod 124 and the spherical object 126 are joined by a connector 128 to the instrument 60, thereby specifying the position and orientation of the instrument 60 with respect to the camera system 10.

Figure 2F:
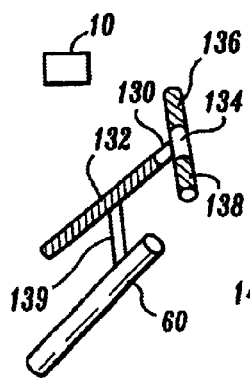

Referring to FIG. 2F, another example of the present invention comprises a longitudinal rod 130 with a reflective linear surface 132 (shaded) and an orthogonal rod 134 with two reflective segments 136 and 138 (shaded). These linear structures again are detectable by the camera system 10, thereby determining the orientation of the plane defined by the longitudinal rod 130 and the orthogonal rod 134. As described above, this is information is then used to determine the orientation and movement of the instrument 60, which is coupled to the rods 132 and 134 via a connector 139, in three-dimensional space.

Figure 2G:
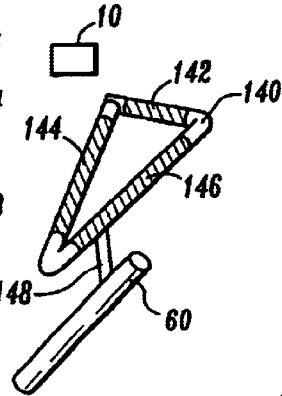

FIG. 2G shows yet another example of rod-like structures in a triangle 140. The shaded linear segments 142, 144, and 146 lie at the edges of the triangle 140 and define the plane and orientation of the triangle 140. The triangle 140 is attached to the instrument 60 by a connector 148, and the instrument is tracked as described above.

Figure 2H:
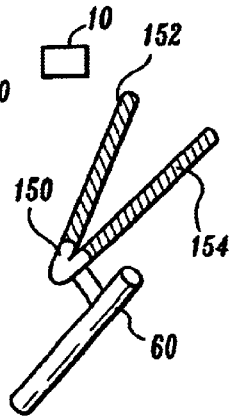

Referring to FIG. 2H, a similar V-shaped structure 150 comprising identifiable leg segments 152 and 154 (shaded) provides a similar position and orientation vector analogous to the previous examples.

FIG. 3 presents several further embodiments of the present invention that are useful in certain applications. In FIG. 3A, a plate 160 or similar structure has detectable areas 162, 164, and 166 (shaded). A connector 168 couples the plate 160 to the instrument 60. In one embodiment of the invention, the plate 160, with its identifiable multiple areas, is a disposable sterile-packed device which can be detachably coupled to the connector 168. The detectable areas 162, 164, and 166 can be, for example, reflective disks that are adhesively affixed to the plate 160 in particular positions that are recognizable and indexed by the camera system 10 in conjunction with the processor 42 and the computer 44 (FIG. 1). The concept of a disposable, single use, sterile-packed, optically detected index marker such as that shown in FIG. 3A has several advantages over non-disposable, more expensive devices. The plate 160 can be coupled to the connector 168 in a pre-calibrated or a non-precalibrated orientation. If calibrated, it will have a known relationship to the instrument 60 and any focal points, features, or directions thereof. If non-precalibrated, the plate 160 could simply be "stuck" onto the connector 168 and used in an intraoperative calibration procedure to determine translations, rotations, and other transformations of the plate 160 and instrument 60 prior to defining the movement and relative orientation of the instrument 60. The process of intraoperatively calibrating positions, directions, and orientations of the instrument 60 is facilitated by an intraoperative calibration holder (not shown; see the products of Radionics, Burlington, Mass.).

Referring to FIG. 3B, another plate-like index structure is shown. A plate 170 is attached to the instrument 60 by a connector 172. On the surface of the plate 170, there are dome-shaped structures 174 and 176. In the disclosed embodiment of the invention, the dome-shaped structures 174 and 176 comprise embedded illumination devices (e.g., LEDs). Alternatively, the dome-shaped structures can include surface-mounted illumination devices, or can simply be made from reflective material. The dome-shaped structures 174 and 176 are then detectable by the camera system 10, as described above. If the dome-shaped structures have spherical or convex surfaces, then the camera system 10 can detect their surfaces and average the three-dimensional positions of the surface points to identify a centroid which may, for example, be the center of a sphere or a hemisphere. Accordingly, there can be several of these spherical or dome-shaped structures on the plate 170 in a pattern or array. The structures can be in a linear array, on the corners of a triangle, on the corners of a square, or in a multiple indexed array to provide position, orientation, and transformation information to a system according to the invention.

Referring to FIG. 3C, yet another plate-like index structure in accordance with the present invention is shown. A plate 180 is attached to the instrument 60 in a similar fashion to that described above. On the surface of the plate 180 are reflective patterns 182 and 184, here in the form of diamonds or other multi-sided objects. Such patterns are identifiable by the camera system 10 and its analysis system to discriminate them from other objects in the field, just as is done in all the previous examples. For example, in the disclosed embodiment, the patterns 182 and 184 are square or diamond-shaped patches of reflective paint or tape; alternatively, they could be brightly colored surfaces with different colors to be detected by the camera system 10. Multiple arrays or groups of such diamond-shaped patterns with differential reflective and non-reflective areas are possible to facilitate discrimination by the camera system 10. For example, a background surface 186 on the plate 180 may be of opaque, black character so that the linear edges between the patterns 182 and 184 and that surface 186, for example, have a sharp optical delineation. This makes it simpler for the camera system 10 and its processor 42, and computer 44 to detect such an edge. If the edge is straight, then detection along the lined contour can readily be performed by well-known analysis methods. This can give precise linear directions which in turn can define the vector and positional orientation of the entire plate 180, and thus the orientation of the instrument 60, with high accuracy.

Referring now to FIG. 3D, yet another plate-like index structure is shown. A plate 190 is shown in a somewhat triangular or trapezoidal shape. It has on it linear structures 191 and 192, which may be reflective edges or other patterns laid down or fastened to the surface plate 190. The linear structures 191 and 192 provide contrast for optical discrimination by being highly reflective or very brightly colored surfaces that are detectable by and analyzable by the camera system 10, as described above. The linear borders on both sides of the structures 191 and 192 make possible linear discrimination analysis of these surfaces and also, by mutual information theory, an easily recognizable pattern. In this case, the pattern is a non-parallel linear or V-shaped pattern of the elements 191 and 192. Such a V-shaped pattern corresponds to and defines two vectors, which in turn can define the plane and orientation of the plate 190, and thus the instrument 60.

In FIG. 3E, the instrument 60 is provided with three spherical elements 193, 194, and 195 in a linear configuration, each of which is made to be reflective or light-emitting. Three centroids corresponding to the spherical elements 193, 194, and 195 can then be determined, and the position and orientation of the instrument 60 follows.

In the embodiment of FIG. 3F, the instrument 60 bears three spherical elements 196, 197, and 198 in a triangular configuration, each of which is reflective, light-emitting, or otherwise optically detectable. The centroids of the three spherical elements 196, 197, and 198 are determinable by the system; the centroids define a plane that specifies the orientation of the instrument 60.

Turning now to FIG. 4, in FIG. 4A a solid three-dimensional optically detectable structure is attached to the instrument 60 or comprises part of the instrument 60 itself. The structure includes a rod 200 which is attached by coupler 202 to a sphere 204. The rod 200 and the sphere 204 comprise reflective or distinctly colored material detectable by the camera system 10. The reflective rod 200 has the advantage that from all directions it has a similar linear shape, the edges of which are discriminated by the camera system 10 and detected by linear edge detection. A centroid axis 206 can therefore be calculated for the rod 200 by the processor 42 and the computer 44 (FIG. 1). The reflective sphere 204 defines a centroid 208 which can be detected by spherical edge detection of the sphere 204 and appropriate centroid calculation in the processor 42 and the computer 44. The combination of the axis 206 and the centroid 208 determines the plane defined by the sphere 204 and the rod 200, and thus the orientation and position of the instrument 60.

In FIG. 4B, a solid prism-shaped object 210 is coupled by a connector 212 to the instrument 60. On the sides of the object 210, namely a right side 214 and a left side 216, there are respective reflective areas 218 and 220 (shaded), which can be polished, painted, reflective paint, or reflective tape surfaces. Their position and direction determine the orientation of the object 210, and therefore by transformation the orientation and position of the instrument 60.

Referring to FIG. 4C, a solid prismoidal structure 222 has distinguishing optically detectable markings which perform as a signature of the instrument 60 to which it is attached. On one face of the structure 222, there is shaded area 224 having a distinct shape. On another face, there are two separate shaded areas 226 and 228 having distinguishable size and shape characteristics. In observing the structure 222, the camera system 10 can determine by the size and shape characteristics of the shaded areas 224, 226, and 228 the orientation and position of the structure 222, and thus the orientation and position of the instrument 60. As described above, a large number of different and identifiable objects such as the structure 222 can be used to distinguish one tool from another. The detectable faces on different sides of the structure 222 will ensure that the structure 222 is identifiable from nearly any direction of view by the camera system 10. Patterns such as bar codes or distinguishable line or object orientations can be used to encode the structure 222 (and thereby the instrument 60), allowing each different type of instrument to be recognizable via pattern recognition algorithms implemented in the processor 42 and the computer 44.

While most of the embodiments described above (in FIGS. 2, 3, and 4) include a connector to couple an optically detectable structure to the surgical instrument 60, it should be noted that the objects, shapes, and patterns in the above examples can generally be built integrally into the instrument 60 itself. The very shape of the instrument may be optically detectable and classified and tracked by the camera system 10 and other processing elements, as described above.

The embodiments of FIGS. 1, 2, 3, and 4 have the advantage of providing optically coupled, non-mechanically coupled, wireless tracking. The marker objects of FIGS. 2, 3, and 4 can be made simply, economically, lightweight, and sterilizable or sterilely packaged. Each embodiment has practical advantages relative to the frame-based or mechanically-linked space pointers given as examples in the background section above.

Figure 5:
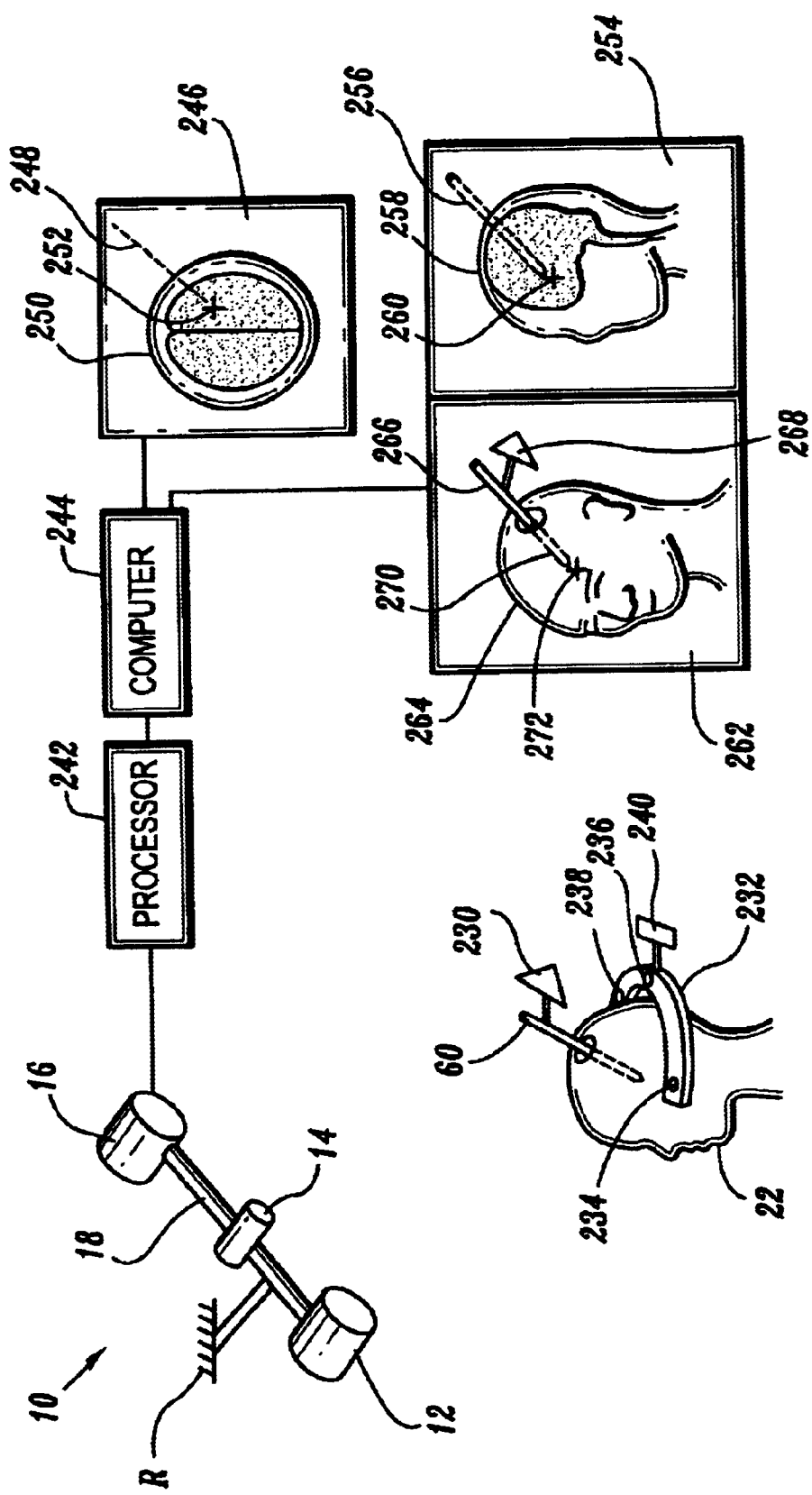
FIG. 5 schematically shows several combinations of graphics, video, and reconstructed representations derived from optically tracking of a surgical field.

FIG. 5 illustrates the operative functionality of a system according to FIG. 1. The surgical instrument 60 has an optically detectable index structure 230. A dynamic referencing head clamp 232 with index marks 234, 236, and 238 is present; the clamp 232 further includes an additional index marker 240. A processor 242 and a computer 244 convert camera data from the camera system 10 for an image display 246, which shows a representation of the position of the instrument 60 as a dashed line 248 relative to an anatomical structure 250. A predetermined point on the instrument 60, such as a tip or a focal point, is indicated relative to the anatomical structure 250 as a point 252. Examples of such coordinated display of probe orientation and image data is given in the product of OTS by Radionics, Burlington, Mass.

The processor 242 and the computer 244 are also capable of generating a separate representation 254 of the position of the instrument 60. The separate representation 254 displays in a two- or three-dimensional form 256 the position of the instrument 60 in comparison to an anatomical rendering 258, along with other optional representations of probe, anatomy, or target points such as a target point 260. In the disclosed embodiment, the separate representation 254 is reconstructed from two-dimensional or three-dimensional image data such as CT or MR scans taken of the patient previously or contemporaneously in a real-time image scanner during surgery or treatment.

As with the system set forth in FIG. 1, three-dimensional analysis of the position of the instrument 60 can be accomplished by determined by the stereoscopic cameras 12 and 16, together with the processor 42 and the computer 44. This can be done based on LED or reflective infrared light processing, or alternatively based on direct visible-light video processing of information from the two cameras 12 and 16. It can be advantageous to provide the cameras 12 and 16 with infrared optical filters. If the optically detectable objects used in the system are infrared LEDs or if the cameras have pulsed infrared light sources near them, then filtering will increase the signal-to-noise ratio of the tracking signal and reduce the effect of any ambient light background.

In an alternative embodiment of the invention, a third camera 14 is provided (see also FIG. 1). The third camera 14 is preferably a standard video camera which views the surgical field. The processor 242 and the computer 244 further display the view from the third video camera 14 in an additional display 262. In this way, a direct video view of the patient 264 is available. In addition, a view of the instrument 60 (seen as an instrument image 266 with an index marker image 268) is seen from actual video.

A virtual extrapolation of the probe, shown as a dashed line 270 with a tip or target point 272, can be determined from the analysis shown on the alternative representation 254. In an embodiment of the invention, this virtual extrapolation is overlaid directly onto the additional display 262 so that direct comparison of the reconstructed three-dimensional navigation image of the alternative representation 254 can be compared to an actual video image on the additional display 262. Correspondence and registration between a reconstructed image and an actual image in this way confirms the correctness of the probe orientation, and consequently the virtual position of unseen elements such as probe tip and probe position, for example in the depths of the surgical wound. Thus, a hybrid of reconstructed stereoscopic tracking by one set of cameras (e.g., the cameras 12 and 16) can be displayed and coordinated with respect to video imaging from another set of cameras (e.g., the video camera 14).

All cameras may be of the visible video type, or some may be filtered infrared (or other spectral filtered types) used with others of the visible video type. For example, in the embodiment of FIG. 5, the cameras 12 and 16 used for tracking are infrared filtered cameras; while the additional video camera 14 observes the visual spectrum. Accordingly, offering a comparison between the views provided by the separate cameras is a useful quality assurance check of the integrity of the entire tracking system.

Figure 6:
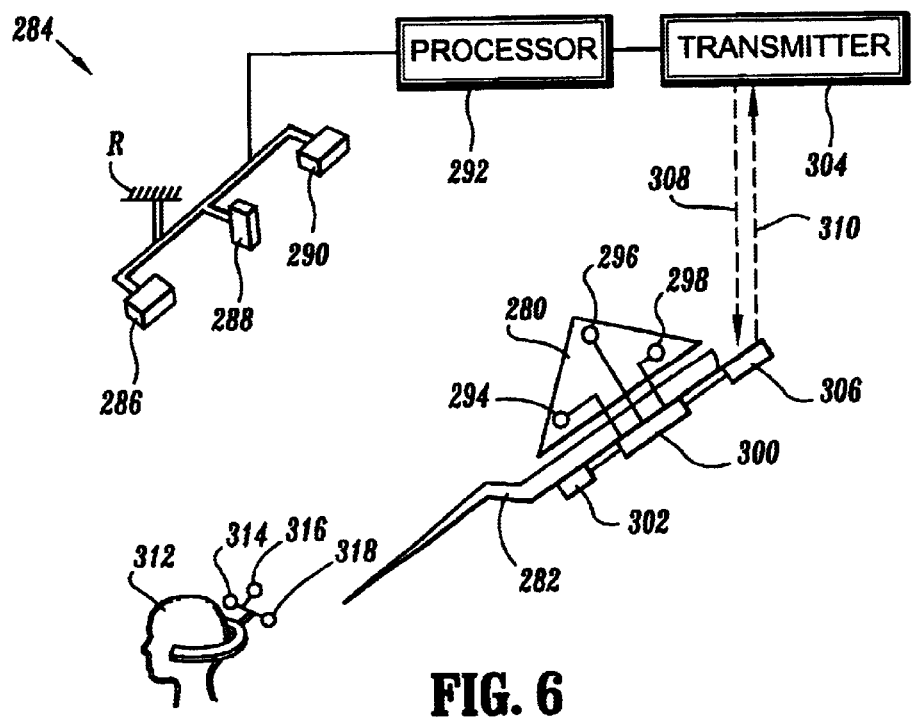
FIG. 6 schematically shows a battery-powered optically tracked instrument for use in accordance with the present invention.

Referring now to FIG. 6, another embodiment of the present invention involves a battery-powered optically detectable index structure 280 associated with an instrument 282. A camera system 284 comprises three cameras 286, 288, and 290, which in the disclosed embodiment are linear infrared CCD cameras (see for example the IGT product, Boulder, Colo.). Data signals are processed by a processor 292, and these can be sent to a computer system, as described above (see FIG. 1). The instrument 282 is shown generically; the optical index structure 280 comprises LED emitters 294, 296, and 298 which in a preferred embodiment are of an infrared-emitting type. The emitters 294, 296, and 298 define a plane of light which can be transformed to specify the position of the instrument 282 to which they are attached. The emitters 294, 296, and 298 are coupled to a circuit 300 which distributes energy to the LEDs for their illumination. The circuit 300 controls the sequence and synchronization of LED lighting. A battery 302 is provided to supply power to the circuit 300 and to the emitters 294, 296, and 298.

In an embodiment of the invention, the LED emitters 294, 296, and 298 are flashed in a coded sequence controlled by the circuit 300 that is detectable by the processor 292 so as to recognize the instrument 282 and the index structure 280. Alternatively, the pattern of positions of the emitters 294, 296, and 298 can be used to allow the processor 292 to discriminate what specific instrument 282 is being used.

As an alternative, a coding scheme can be sent from a transmitter 304 to a receiver 306 coupled to the instrument 282. The receiver 306 accepts light or radio wave signals from the transmitter 304, which is connected to the processor 292. A synchronization signal representative of the shutter operation from the cameras 286, 288, and 290 is sent via the transmitter 304 (as shown by a dashed line 308) to the receiver 306. The receiver 306 and the circuit 300 then cause the sequential flashing of the emitters 294, 296, and 298 detected by the cameras. An optional return signal (represented by a dashed line 310) from the receiver 306 to the transmitter 304 can be used to confirm the synchronization of the emitters to the cameras.

Again a patient 312 may be in the surgical field with attached optically detectable index elements 314, 316, and 318, plus others as described above. These light emitters may also be battery powered or wire powered from either batteries or another source.

The LED emitters 294, 296, and 298 do not consume much power if they are flashed intermittently, and thus the battery 302 comprises a standard type of battery, such as one that might be used to operate a flashlight, camera, or other small appliance. Such batteries can easily be replaced or sterilized at the time of surgery. The use of batteries in a surgical instrument is advantageous in that the system is wireless and mechanically de-coupled from the camera system and its processor.

Referring again to FIG. 1, light sources may be used near to the cameras to produce reflected light from reflecting optically-detectable objects. In various embodiments of the invention, the optically detectable objects can alternatively have bright, colored, or shiny surfaces or have contrasting patterns of light and dark or alternately colored shapes and patterns to be detectable by cameras in ambient light. By arranging the ambient light to shine appropriately on a surgical, diagnostic, or therapeutic setting, objects can be recognized directly by the camera system 10 as shown in FIG. 1. However, the use of additional lights near the cameras can enhance the reflection from optically detectable objects in certain clinical settings where ambient light may not be sufficient, or where high degrees of light contrast, such as from surgical head holders, microscope lights, or operating theatre lights may cause difficulty in discriminating light levels from the detectable objects. Thus, various illumination possibilities can easily be devised in accordance with the present invention to facilitate detection and data processing of the camera and video information to suit the clinical context.

Figure 7:
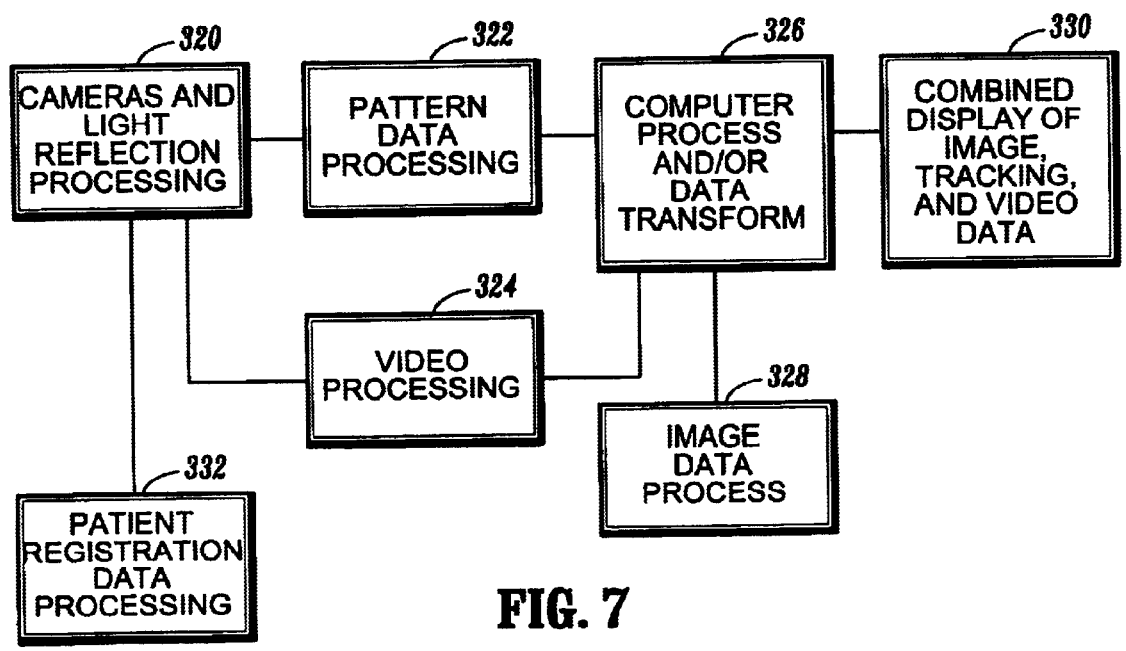
FIG. 7 illustrates the functions performed in the combined processing of tracking, videos, and/or image data in a display in accordance with the present invention.

Referring now to FIG. 7, a block diagram is provided to illustrate the relationship among the various functional steps performed by a system according to the invention. A camera and light reflection processing function (block 200) specifies that the camera system 10 (FIG. 1) detects an instrument with an optically detectable object attached to it. This is done with a camera system as described above, wherein camera data from infrared filtered cameras of various kinds and/or video cameras is provided to a pattern data processing function (block 322). The pattern data processing function 322 receives data from the camera and light reflection processing function 320, allowing the instrument is recognized by pattern recognition algorithms operating on stereoscopic data received from the camera system 10. The nature of the instrument can also be recognized by way of time or geometric sequencing or arrangements of light-emitting or light reflecting objects or patterns on the instrument, as described above.

Referring now to FIG. 7, a block diagram is provided to illustrate the relationship among the various functional steps performed by a system according to the invention. A camera and light reflection processing function (block 320) specifies that the camera system 10 (FIG. 1) detects an instrument with an optically detectable object attached to it. This is done with a camera system as described above, wherein camera data from infrared filtered cameras of various kinds and/or video cameras is provided to a pattern data processing function (block 322). The pattern data processing function 322 receives data from the camera and light reflection processing function 320, allowing the instrument is recognized by pattern recognition algorithms operating on stereoscopic data received from the camera system 10. The nature of the instrument can also be recognized by way of time or geometric sequencing or arrangements of light-emitting or light reflecting objects or patterns on the instrument, as described above.

Various examples of combination displays have been described in connection with FIG. 5. A useful quality assurance check would be, for example, to overlay visible video data onto the combined representations of the image scan data and of the surgical instrument as it moves relative to the anatomy. The video data shows in real time the position of an instrument relative to the anatomy, or the relative position of instruments relative to each other, within the field of surgical view. Seen on a display, a rendering of the reconstructed position of a surgical instrument relative to the overlaid anatomy, or compared side-by-side to the actual visible video view of the instrument relative to the anatomy, is a strong confirmational step to show that the tracking is being done properly. In certain clinical situations such as surgery, X-ray treatment on a treatment planning machine such as a linear accelerator, or patient positioning on a diagnostic machine, such a confirmational step could be very important. Thus, the process of FIG. 7 can apply to camera and video detection in the surgical setting, a diagnostic suite, or in connection with treatment planning process and instrumentation. Use, for example, together with a real time diagnostic or intraoperative imaging machine such as a CT, MR, PET, X-ray, or other scanner would be another context for the process in FIG. 7.

Also shown in FIG. 7 is a patient registration data processing function (block 332), which represents the step of registering or calibrating instrumentation or apparatus relative to a patient, prior to performing a procedure with the tracked instrument. The registration step may be predetermined or determined during the clinical setting in a variety of ways, as described above.

Figure 8:
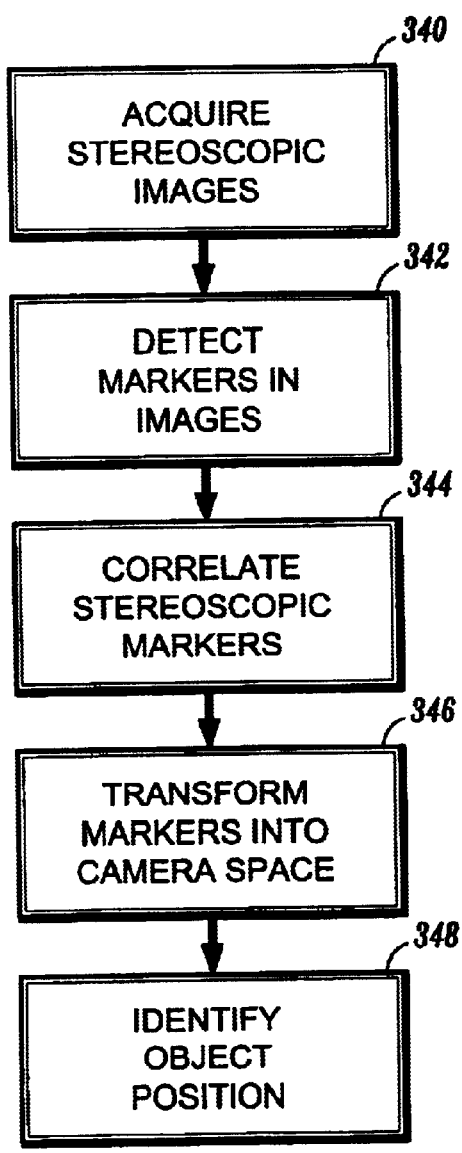
FIG. 8 is a flowchart showing the sequence of steps performed in tracking an optically detectable object.

The steps performed in tracking an object (for example, the instrument 60, the patient 22, or the surgeon 76) according to the invention are set forth in FIG. 8. First, a set of multiple camera images (stereoscopic images for the case of two or more two-dimensional cameras) is acquired (step 340) from the camera system 10 (FIG. 1). Any markers present in the stereoscopic images are then detected (step 342) as described above. For example, when two two-dimensional CCD cameras are used, there are two frames in a set of stereoscopic images, namely a left frame (from the left camera 16) and a right frame (from the right camera 12). The detected markers will appear in slightly different positions in the two frames, so the positions are then correlated (step 344). The difference in a marker's position between the two frames is used to determine depth (i.e., distance from the camera system 10) in three dimensions. It should be noted that more than two cameras may be used in the present invention; the additional cameras can be used to verify the stereoscopic images or to provide further accuracy or definition.

After the markers have been correlated between the stereoscopic frames, the images are further processed to determine the positions of the markers in three-dimensional space by transforming the markers (step 346) into a coordinate system defined by the camera system 10. As described above, this step is performed in varying ways depending on the nature of the markers in the field of view. For example, a spherical marker will define a centroid, while a rod-shaped or flat marker will define an axis. Accordingly, the unique set of centroids, axes, and other characteristics in the coordinate system of the cameras can be used to identify the position of the object being tracked (step 348). This information is used in the operation of the system as described below.

Figure 9:
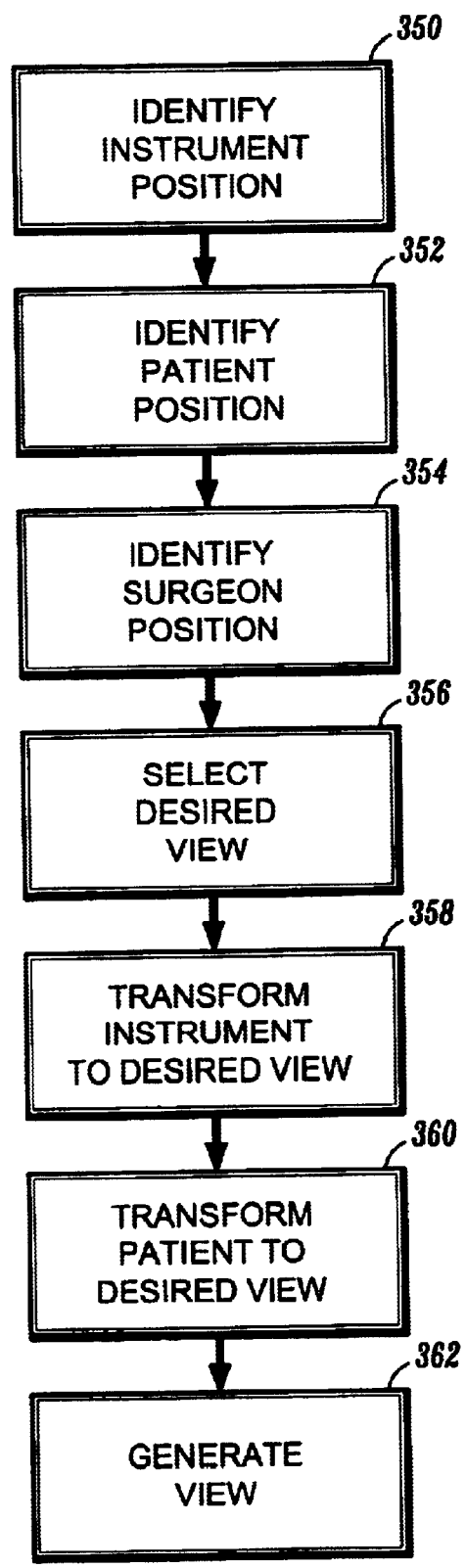
FIG. 9 is a flowchart illustrating the sequence of steps performed in generating a display when a surgical instrument, a patient, and a surgeon are all tracked by a system in accordance with the invention.

FIG. 9 illustrates, in one exemplary embodiment, how the various objects are tracked by the system to generate one or more displays, as described above. First, the location of the surgical instrument 60 (FIG. 1) is identified (step 350) with respect to the camera system 10, as described in conjunction with FIG. 8. A set of coordinates is generated thereby. Those coordinates specify the position of the instrument 60, and further specify a transformation between the coordinate system of the camera system 10 and a coordinate system associated with the instrument. This may involve, for example, index point registrations from the patient's physical anatomy to image scan data, as described previously. Next, or concurrently, the location of the patient 22 is identified (step 352) with respect to the camera system 10. Again, the coordinates specify the position of the patient 22 and a coordinate transformation between the camera system and the patient. Finally, or concurrently, the location of the surgeon 76 is identified (step 354), as above.

With all of the positional data having been generated, a desired view is selected (step 356) by the surgeon or other operator. Several possible views have been described above, but there are alternatives. For example, a "surgeon's eye" view is possible by transforming the instrument position and the patient position into the surgeon's coordinate system. An "instrument's eye" view is possible by transforming the patient position into the instrument's coordinate system. A patient-centered system is possible by transforming the instrument position into the patient's coordinate system. These transformations involve simple matrix manipulation and trigonometric calculations; they would be well-known to a person of ordinary skill in the mathematical arts.

The desired transformations of the instrument position (step 358) and the patient position (step 360) are then performed. A display is generated (step 362) based on the transformed positions (see FIG. 5). As described above, the display can comprise only a reproduction of the instrument in relation to a reproduction of the patient's anatomical structures (for example, based on reconstructions from image scan data from CT, MR, or other types of scans), or can include an overlaid video view from a video camera 14 on the camera system 10 or a video camera 82 on the surgeon 76. Moreover, the patient's anatomical data can be manipulated in various ways well known in the art to provide slice, cutaway, or contour views, among others. Moreover, further coordinate transformations can optionally be provided to allow operator control over the views on the display, for example to slightly displace a view from a true "instrument's eye" view.

Steps 350–362 are repeated as necessary to update the display with the various object positions in real time or close to real time.

Forms and embodiments of optical object tracking systems and methods are provided involving various geometries, detection methods, pattern recognition methods, display methods, systems components, and process steps. However, it should be recognized that other forms varying from the embodiments specifically set forth herein may be used as variations of the above examples in accordance with the present invention. In particular, it should be noted that although various functional components have been set forth and described herein, many of these functional components can be integrated (into a single general-purpose digital computer, for example), or performed by separate processing devices; any such embodiment is intended to be within the scope of the invention. Moreover, although sequences of process steps are set forth herein as though performed in a certain order, it is recognized that the invention will be equally operative if the steps are rearranged or otherwise performed in a different order. In addition, it has been noted that certain steps are optional, such as identifying the surgeon's position (step 354) if it is not desired to track the surgeon.

In view of these considerations, as would be apparent by persons skilled in the art, the implementation of a system in accordance with the invention should be considered broadly and with respect to the claims set forth below.

What is claimed is:

1. A system for optically tracking an instrument relative to the anatomy of a patient in a clinical field of view, comprising:
    a camera system including at least two spatially separated cameras, capable of viewing the clinical field of view to provide camera data in a first coordinate system defined by the camera system;
    an instrument comprising an optically detectable object that is detectable by the camera system to provide instrument data representative of the position of the instrument in the first coordinate system;
    a headband positionable on the head of a surgeon, the headband including a display viewable by the surgeon and an optically detectable array that is detectable by the camera system to provide headband data representative of the position of the headband in the first coordinate system;
    data storage comprising one of CT and MRI image data representative of the anatomy of the patient received from one of a CT and MRI imaging machine; and
    a computer to accept the camera data, the instrument data, the headband data, and the image data, and being programmed to transform the image data, the camera data, the headband data, and the instrument data into a second coordinate system, thereby generating tracking data representative of the position of the instrument and the headband in relation to the anatomy of the patient.

2. The system of claim 1, wherein the first coordinate system is identical to the second coordinate system.

3. The system of claim 2, wherein:
    each camera in the camera system has a filter passing the infrared optical spectrum; and
    the optically detectable object is visible in the infrared spectrum.

4. The system of claim 3, wherein said optically detectable object comprises an emitter of infrared light.

5. The system of claim 3, further comprising at least one infrared light source, and wherein the optically detectable object comprises a reflective object; whereby infrared light emitted from the infrared light source is reflected from the optically detectable object toward the camera system.

6. The system of claim 2, wherein said optically detectable array includes light-emitting indicators.

7. The system of claim 6, wherein said headband includes at least one video camera.

8. The system of claim 1 wherein the camera system comprises at least two two-dimensional CCD cameras.

9. The system of claim 1, wherein the camera system comprises at least three linear CCD cameras.

10. The system of claim 1, wherein the optically detectable object comprises an arrangement of geometric objects identifiable by said camera system to yield position data representative of the position of the optically detectable object.

11. The system of claim 10, wherein the arrangement of geometric objects comprises a pattern of light-emitting diodes (LEDs).

12. The system of claim 10, wherein the arrangement of geometric objects comprises at least one optically detectable rod.

13. The system of claim 10, wherein the arrangement of geometric objects comprises at least one optically detectable rod and at least one optically detectable sphere.

14. The system of claim 10, wherein the arrangement of geometric objects comprises a pattern of optically detectable geometric forms disposed on a surface.

15. The system of claim 14, wherein the surface comprises a substantially planar plate and the geometric forms comprise a plurality of linear shapes defining an orientation of the optically detectable object.

16. The system of claim 14, wherein the geometric forms comprise at least one circular shape.

17. The system of claim 10, wherein the arrangement of geometric objects comprises at least one sphere.

18. The system of claim 17, wherein the arrangement of geometric objects comprises three spheres.

19. The system of claim 10, wherein the arrangement of geometric objects comprises a plurality of surfaces bearing reflective material.

20. The system of claim 10, wherein the arrangement of geometric objects comprises a plurality of surfaces bearing brightly colored material.

21. The system of claim 10, wherein the arrangement of geometric objects comprises a plurality of illuminated surfaces.

22. A method for providing a reconstructed view of a surgical field, comprising the steps of:
    tracking the position and orientation of a surgical instrument with a camera system;
    tracking the position and orientation of a patient with the camera system;
    tracking the position and orientation of a surgeon with the camera system and a headband including an optically detectable array and a video camera;
    transforming the position and orientation of the surgical instrument into a desired coordinate system;
    transforming the position and orientation of the patient into the desired coordinate system;
    transforming the position and orientation of the surgeon into the desired coordinate system;
    retrieving stored image data representative of the patient's anatomy;
    transforming said stored image data into the desired coordinate system;
    generating a video view of the surgical field using the video camera;
    generating the reconstructed view of the surgical field in relation to the surgeon using the transformed stored image data in the desired coordinate system; and
    displaying a representation of the surgical instrument with respect to a representation of the patient and the surgeon in the desired coordinate system.

23. The method of claim 22, further comprising the step of overlaying the reconstructed view of the surgical field with the video view received from the video camera.

24. The method of claim 23, wherein a second video camera is mounted to the camera system.

25. The method of claim 23, wherein the video camera is mounted to the surgeon.

26. The method of claim 22, wherein the displaying step delivers the reconstructed view of the surgical field to a video monitor.

27. The method of claim 22, wherein the displaying step delivers the reconstructed view to a headset worn by a surgeon.

28. A system for optically tracking an instrument relative to the anatomy of a patient in a clinical field of view, comprising:

a camera system including at least two spatially separated cameras, capable of viewing the clinical field of view to provide camera data in a first coordinate system defined by the camera system;

an instrument comprising an optically detectable object that is detectable by the camera system to provide instrument data representative of the position of the instrument in the first coordinate system;

a headband positionable on the head of a surgeon, the headband including an optically detectable array and at least one video camera, said optically detectable array including light-emitting diodes and being detectable by the camera system to provide headband data representative of the position of the headband in the first coordinate system;

data storage comprising image data representative of the anatomy of the patient received from an imaging machine; and a computer to accept the camera data, the instrument data, the headband data, and the image data, and being programmed to transform the image data, the camera data, the headband data, and the instrument data into a second coordinate system, the second coordinate system being identical to the first coordinate system, thereby generating tracking data representative of the position of the instrument and the headband in relation to the anatomy of the patient.

29. The system of claim 28, further comprising a display to display the tracking data.

30. The system of claim 28, wherein the camera system comprises at least two two-dimensional CCD cameras.

31. The system of claim 28, wherein the camera system comprises at least three linear CCD cameras.

32. The system of claim 28, wherein each camera in the camera system has a filter passing the infrared optical spectrum and the optically detectable object is visible in the infrared spectrum.

33. The system of claim 32, wherein said optically detectable object comprises an emitter of infrared light.

34. The system of claim 32, further comprising at least one infrared light source, and wherein the optically detectable object comprises a reflective object; whereby infrared light emitted from the infrared light source is reflected from the optically detectable object toward the camera system.

35. The system of claim 28, wherein the optically detectable object comprises an arrangement of geometric objects identifiable by said camera system to yield position data representative of the position of the optically detectable object.

36. The system of claim 35, wherein the arrangement of geometric objects comprises a pattern of light-emitting diodes.

37. The system of claim 35, wherein the arrangement of geometric objects comprises at least one optically detectable rod.

38. The system of claim 35, wherein the arrangement of geometric objects comprises at least one optically detectable rod and at least one optically detectable sphere.

39. The system of claim 35, wherein the arrangement of geometric objects comprises a pattern of optically detectable geometric forms disposed on a surface.

40. The system of claim 39, wherein the surface comprises a substantially planar plate and the geometric forms comprise a plurality of linear shapes defining an orientation of the optically detectable object.

41. The system of claim 39, wherein the geometric forms comprise at least one circular shape.

42. The system of claim 35, wherein the arrangement of geometric objects comprises at least one sphere.

43. The system of claim 42, wherein the arrangement of geometric objects comprises three spheres.

44. The system of claim 35, wherein the arrangement of geometric objects comprises a plurality of surfaces bearing brightly colored material.

45. The system of claim 35, wherein the arrangement of geometric objects comprises a plurality of illuminated surfaces.

46. A method for providing a reconstructed view of a surgical field, comprising the steps of:

tracking the position and orientation of a surgical instrument with a camera system;

tracking the position and orientation of a patient with the camera system;

tracking the position and orientation of a surgeon with the camera system;

transforming the position and orientation of the surgical instrument into a desired coordinate system;

transforming the position and orientation of the patient into the desired coordinate system;

transforming the position and orientation of the surgeon into the desired coordinate system;

retrieving stored image data representative of the patient's anatomy;

transforming said stored image data into the desired coordinate system;

generating the reconstructed view of the surgical field in relation to the surgeon using the stored image data in the desired coordinate system;

overlaying the reconstructed view of the surgical field with a video view received from a video camera;

displaying a representation of the surgical instrument with respect to a representation of the patient and the surgeon in the desired coordinate system; and displaying the reconstructed view of the surgical field to a headset worn by the surgeon.

47. The method of claim 46, wherein the video camera is mounted to the camera system.

48. The method of claim 46, wherein the video camera is mounted to the surgeon.

49. The method of claim 46, wherein the displaying step delivers the reconstructed view of the surgical field to a video monitor.

* * * * *